United States Patent
Harms et al.

(10) Patent No.: US 9,724,480 B2
(45) Date of Patent: Aug. 8, 2017

(54) DRUG DELIVERY DEVICE (71) Applicant: Sanofi-Aventis Deutschland GmbH, Frankfurt am Main (DE)

(72) Inventors: Michael Harms, Frankfurt am Main (DE); Verena Hofmann, Frankfurt am Main (DE); Gareth Roberts, Wrexham (GB); Chris Ward, Prestatyn (GB); Graham Wilson, Flintshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/414,671

(22) PCT Filed: Jul. 17, 2013

(86) PCT No.: PCT/EP2013/065130
§ 371 (c)(1),
(2) Date: Jan. 13, 2015

(87) PCT Pub. No.: WO2014/012996
PCT Pub. Date: Jan. 23, 2014

(65) Prior Publication Data
US 2015/0202380 A1    Jul. 23, 2015

Related U.S. Application Data (60) Provisional application No. 61/715,159, filed on Oct. 17, 2012.

(30) Foreign Application Priority Data

Jul. 17, 2012 (EP) ..................................... 12176675

(51) Int. Cl.
*A61M 5/32* (2006.01)
*A61M 5/46* (2006.01)

(52) U.S. Cl.
CPC .......... *A61M 5/3272* (2013.01); *A61M 5/326* (2013.01); *A61M 5/3204* (2013.01);
(Continued)

(58) Field of Classification Search
CPC .............. A61M 5/3202; A61M 5/3243; A61M 5/3257; A61M 5/3271; A61M 5/3272;
(Continued)

(56) References Cited

U.S. PATENT DOCUMENTS 4,955,872 A * 9/1990 Callaway ................. A61M 5/34
604/272
5,242,401 A * 9/1993 Colsky .................. A61M 5/326
604/110

(Continued)

FOREIGN PATENT DOCUMENTS

CN       1076371       9/1993
EP    WO2012/055839 A2 *  5/2012   .......... A61M 5/3257
(Continued)

OTHER PUBLICATIONS

Chinese Office Action in Chinese Application No. 201380037581. X, dated Sep. 26, 2016, 6 pages.
(Continued)

*Primary Examiner* — Imani Hayman
*Assistant Examiner* — James D Ponton
(74) *Attorney, Agent, or Firm* — Fish & Richardson P. C.

(57) ABSTRACT

The invention relates to a drug delivery device for setting and dispensing a dose of a drug, comprising: a support body having a first end defining a first opening and a second end defining a second opening, the support body configured to retain a syringe barrel sealed by a stopper slidably disposed therein along an axial direction and adapted to have an integrated needle or to be coupled with a needle assembly, a needle shield adapted to be coupled to one of the ends of
(Continued)

the support body, slidably disposed thereon and keyed to the support body for preventing relative rotation, wherein at least one guiding track is defined on the support body and at least one retaining clip arranged on the needle shield is deflectable by the guiding track, wherein the guiding track is configured such that the retaining clip follows a first path when the needle shield is depressed from an extended position to a retracted position for needle extension and that the retaining clip follows a different second path when the needle shield is subsequently extended, wherein a non-return catch is arranged for catching the retaining clip at the end of the second path.

19 Claims, 5 Drawing Sheets

(52) U.S. Cl.
CPC ............. *A61M 5/3287* (2013.01); *A61M 5/46* (2013.01); *A61M 2005/3247* (2013.01); *A61M 2005/3267* (2013.01); *A61M 2205/582* (2013.01); *A61M 2205/583* (2013.01); *A61M 2205/586* (2013.01)

(58) Field of Classification Search
CPC .. A61M 2005/3247; A61M 2005/3267; A61M 2005/2013; A61M 2005/208
See application file for complete search history.

(56) References Cited

U.S. PATENT DOCUMENTS

| | | |
|---|---|---|
| 5,295,965 A | 3/1994 | Wilmot |
| 2007/0106225 A1* | 5/2007 | Millerd ............... A61M 5/3202 604/198 |
| 2009/0024093 A1 | 1/2009 | Carrel et al. |
| 2012/0130316 A1* | 5/2012 | Boyd ...................... A61M 5/24 604/189 |
| 2012/0316508 A1* | 12/2012 | Kirchhofer ....... A61M 5/31553 604/198 |
| 2013/0023822 A1* | 1/2013 | Edwards ............. A61M 5/2033 604/82 |

FOREIGN PATENT DOCUMENTS

| | | |
|---|---|---|
| WO | 2011075524 A1 | 6/2011 |
| WO | 2012000834 A1 | 1/2012 |

OTHER PUBLICATIONS

International Preliminary Report on Patentability in International Application No. PCT/EP2013/065130, dated Jan. 20, 2015, 8 pages.
International Search Report and Written Opinion in International Application No. PCT/EP2013/065130, dated Oct. 8, 2013, 12 pages.

* cited by examiner

DRUG DELIVERY DEVICE

CROSS REFERENCE TO RELATED APPLICATIONS

The present application is a U.S. National Phase Application pursuant to 35 U.S.C. §371 of International Application No. PCT/EP2013/065130 filed Jul. 17, 2013, which claims priority to European Patent Application No. 12176675.2 filed Jul. 17, 2012 and U.S. Provisional Patent Application No. 61/715,159 filed Oct. 17, 2012. The entire disclosure contents of these applications are herewith incorporated by reference into the present application.

FIELD OF INVENTION

The present invention relates to drug delivery device with inherent needle safety comprising a pre-filled syringe.

BACKGROUND

Pre-filled syringes that are filled with a selected dosage of a medicament are well known injection devices for administering the medicament to a patient. Drug delivery devices comprising a needle shield for covering a needle of a pre-filled syringe before and after use are also well known. Typically, the needle shield is either manually moved or moved by the action of a relaxing spring to surround the needle.

A different type of drug delivery device known in the state of the art solves the object of providing needle safety by arranging the pre-filled syringe movable relative to a body, whereas the pre-filled syringe is retracted into the body after the injection.

SUMMARY

It is an object of the present invention to provide an improved drug delivery device.

The object is achieved by a drug delivery device according to claim 1.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention a drug delivery device for setting and dispensing a dose of a drug comprises:
  a support body having a first end defining a first opening and a second end defining a second opening, the support body configured to retain a syringe barrel sealed by a stopper slidably disposed therein along an axial direction and adapted to have an integrated needle or to be coupled with a needle assembly,
  a needle shield adapted to be coupled to one of the ends of the support body, slidably disposed thereon and keyed to the support body for preventing relative rotation,
  wherein at least one guiding track is defined on the support body and at least one retaining clip arranged on the needle shield is deflectable by the guiding track, wherein the guiding track is configured such that the retaining clip follows a first path when the needle shield is depressed from an extended position to a retracted position for needle extension and that the retaining clip follows a different second path when the needle shield is subsequently extended, wherein a non-return catch is arranged for catching the retaining clip at the end of the second path.

Hence, the retaining clips allow for retracting the needle shield once in order to insert the needle into an injection site. If the drug delivery device is subsequently removed from the injection site, the needle shield re-extends or is allowed to re-extend for covering the needle, whereby the retaining clips will relax into the catch thus locking the needle shield in position relative to the support body. Hence, the needle shield is prevented from being depressed once more without destroying the drug delivery device.

The drug delivery device according to the invention is particularly short and has a low part count.

In an exemplary embodiment the second path is defined by a proximal inclined section of the guiding track for deflecting the retaining clip from a relaxed position in a tangential direction, wherein the catch is arranged distally from the proximal inclined section in a manner allowing the retaining clip to relax into the catch.

In an exemplary embodiment the first path is defined at least by a distal inclined section of the guiding track for deflecting the retaining clip in a different tangential direction thus providing a detent force which has to be overcome in order to retract the needle shield. The distal inclined section and the retaining clip may therefore be referred to as a second detent mechanism arranged to constrain movement of the needle shield relative to the support body by opposing this movement with a second detent force. This prevents inadvertent exposure of the needle by shaking or reversing the drug delivery device prior to application against the injection site.

However, the second detent does not necessarily have to be integrated with the guiding track and retaining clip. Instead, the second detent mechanism may be separately arranged.

In an exemplary embodiment a longitudinal section may arranged proximally from the distal inclined section for defining the first path.

In an exemplary embodiment an outer body may be adapted to be coupled to the other end of the support body and slidably disposed thereon.

A plunger rod may be coupled to the stopper, wherein a proximal portion of the plunger rod is adapted to be coupled to the outer body such that the plunger and stopper can be displaced by depression of the outer body with respect to the support body.

In an exemplary embodiment a first detent mechanism may be arranged to constrain movement of the outer body relative to the support body by opposing this movement with a first detent force. This avoids a so called wet injection with drug leaking out of the tip of the needle during needle insertion before reaching the insertion depth.

In an exemplary embodiment the first detent force is greater than a sum of the second detent force and a counteracting force of a needle shield spring arranged to bias the needle shield against the support body. This allows for a phased movement of the drug delivery device. When applied against the injection site the needle shield will move first for inserting the needle into the injection site. On further application of force the outer body moves for delivering the drug.

In an exemplary embodiment the support body may have a first end defining a first opening and a second end defining a second opening and a centered outer indicator ring arranged to limit the movement of the outer body as well as of the needle shield with respect to the support body.

In an exemplary embodiment the outer indicator ring is designed as a circumferential rib. Alternatively, the outer indicator ring may be designed as at least one circumferential rib section.

In an exemplary embodiment the outer indicator ring may be curved.

The support body may comprise outer guiding means protruding radially outwards for guiding the movement of the outer body or the support body may comprise a guiding slot disposed within the wall of the support body for guiding the movement of the needle shield. The support body and outer body are thus keyed and prevented from rotating independently.

The needle shield may be arranged as one part or it may comprise at least a body section and a cap part. The cap part of the needle shield is rotationally locked to the body section. This may be achieved by the cap part having a non-circular, e.g. elliptical cross section engaging in a corresponding opening in the body section.

In an exemplary embodiment the outer body may be formed as a single part or the outer body may comprise at least a base section and a cap part.

The plunger rod may comprise a flange to engage a barrel collar of the syringe barrel.

The end of the outer body coupled to the support body may comprise a radially outwards directed flange thus improving ergonomics when applying the drug delivery device.

In an exemplary embodiment a direction indicator designed as a profiled cavity or concavity in the surface of the outer body may be arranged in the range of the flange.

The needle shield may likewise comprise a direction indicator.

The ends of the outer body and the needle shield coupled to the support body may have mating surfaces. Mating surfaces, particularly also mating with the shape of the indicator ring visually and haptically indicate to the user that the respective parts are intended to be pushed completely together so that the mating parts abut in order to correctly apply the drug delivery device.

The support body may comprise a radially inwards-directed rib to retain the barrel collar thus fixing the syringe barrel in axial translation with respect to the support body.

The length of the support body may approximately correspond with the combined length of the outer body and the needle shield.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
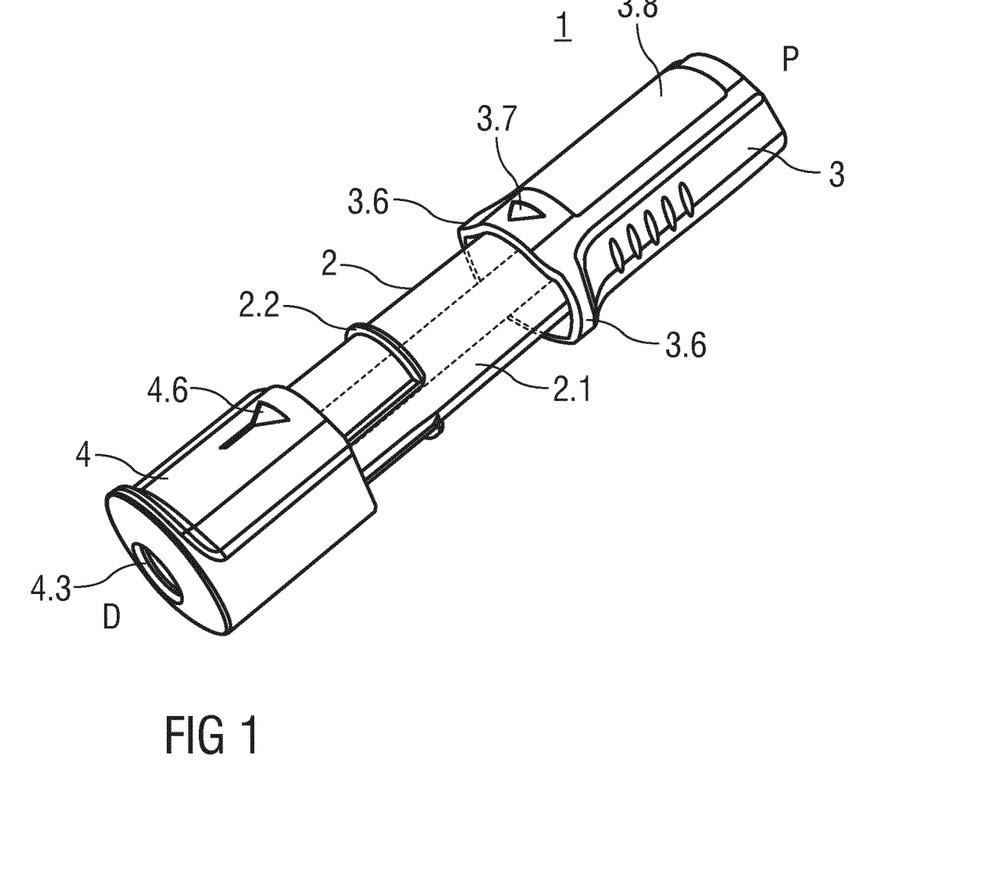
FIG. 1 is a perspective view of a drug delivery device comprising a support body, an outer body and a needle shield.
Figure 2:
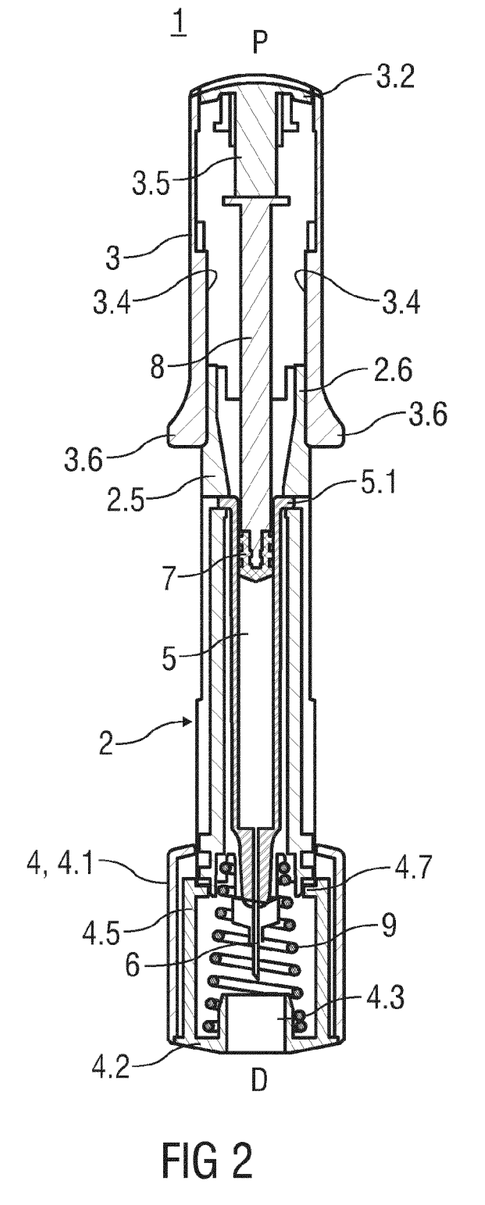
FIG. 2 is a longitudinal section of the drug delivery device in a first section plane.
Figure 3:
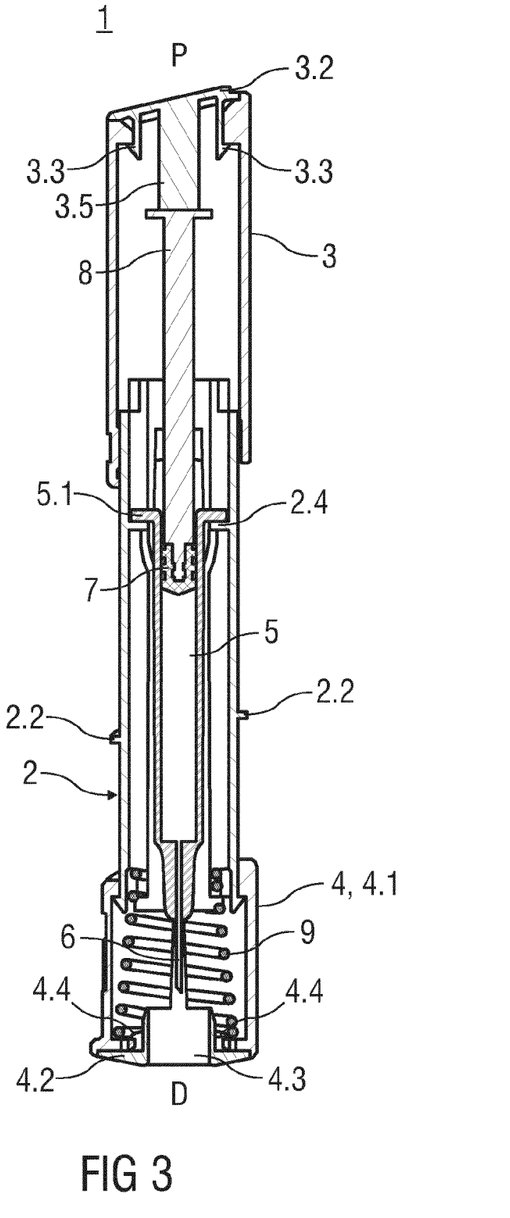
FIG. 3 is a longitudinal section of the drug delivery device in a second section plane.

FIG. 1 is a perspective view of a drug delivery device 1 comprising a support body 2, an outer body 3 and a needle shield 4, all of them having an essentially tubular shape. FIG. 2 is a longitudinal section of the drug delivery device 1 in a first section plane. FIG. 3 is another longitudinal section of the drug delivery device 1 in a second section plane approximately 90° offset from the section plane in FIG. 2. A proximal end of the support body 2 is telescoped in the outer body 3 and a distal end of the support body 2 is telescoped in the needle shield 4. A syringe barrel 5 is slidably arranged within the support body 2, the syringe barrel 5 defining an inner cavity for a dose of a drug. A hollow injection needle 6 is arranged on a distal end of the syringe barrel 5. A stopper 7 is slidably arranged within the syringe barrel 5 for sealing its proximal end and for displacing the drug from the syringe barrel 5 through the injection needle 6. A plunger rod 8 is arranged within the outer body 2 for engaging the stopper 7. The plunger rod 8 may be screwed or snapped into the stopper 7. A needle shield spring 9 is arranged for biasing the needle shield 4 in the distal direction D against the support body 2.

Figure 4:
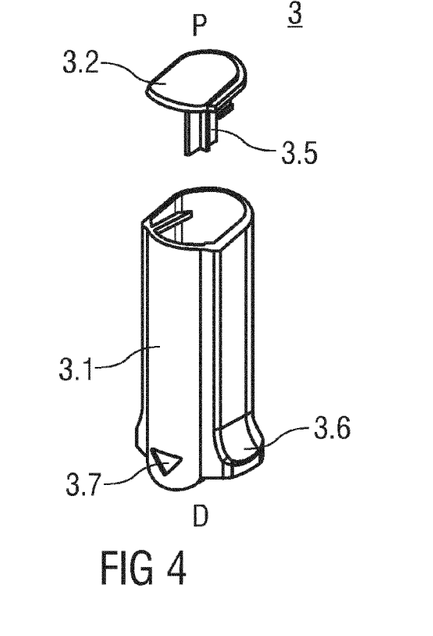
FIG. 4 is an exploded perspective view of the outer body.

FIG. 4 is an exploded perspective view of the outer body 3. The outer body 3 comprises a tubular base section 3.1 and a cap part 3.2 for closing the proximal end of the base section 3.1. The cap part 3.2 is engageable to the base section 3.1 by a snap fit 3.3 (cf. FIG. 3). The base section 3.1 comprises two ribs 3.4 (cf. FIG. 2) extending inwardly from an inner surface of the base section 3.1 on opposite sides for respectively sliding along a guiding slot 2.1 in the support body (cf. FIG. 1). The cap part 3.2 has a central peg 3.5 for engaging the plunger rod 8 when the drug delivery device 1 is assembled. The central peg 3.5 may either abut the plunger rod 8 or be attached to it. The outer body 3 is movable in a distal direction D and in a proximal direction P with respect to the support body 2.

The syringe barrel 5 is inserted into the support body 2. A proximal barrel collar 5.1, sometimes referred to as a finger flange, on the syringe barrel 5 serves for attaching the syringe barrel 5 to the support body 2 by distally abutting an internal rib 2.4 in the support body 2 so that the syringe barrel 5 is fixed towards the distal direction D in its axial position with respect to the support body 2. The syringe barrel 5 is also fixed towards the proximal direction P by two resilient non-return clips 2.5 which are deflected by the barrel collar 5.1 when assembling the syringe barrel 5 into the support body 2 and snap in place once the barrel collar 5.1 has passed them thus facilitating assembly.

Figure 5:
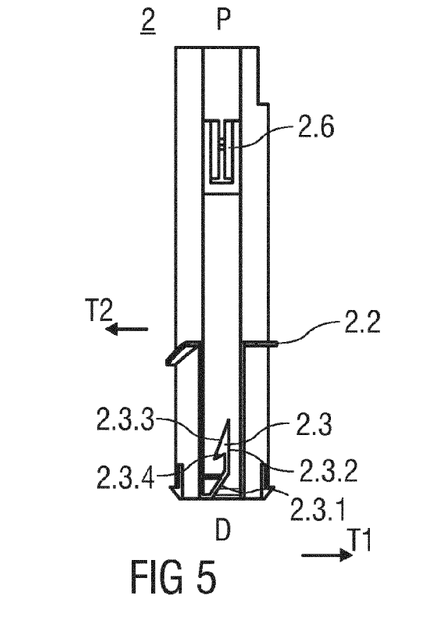
FIG. 5 is a longitudinal section of the support body.

FIG. 5 is a longitudinal section of the support body 2. The support body 2 comprises a indicator ring 2.2 in the shape of radially outwards protruding and essentially circumferential rib. The indicator ring 2.2 may cover part of or the whole circumference of the support body 2. The indicator ring 2.2 is arranged to interact with the needle shield 4 so as to limit distal movement of the support body 2 with respect to the needle shield 4. A guiding track 2.3 is arranged in an outer surface of the support body 2 at the distal end for interacting with the needle shield 4 for limiting axial movement of the support body 2 with respect to the needle shield 4. The guiding track 2.3 comprises a distal inclined section 2.3.1, a longitudinal section 2.3.2, a proximal inclined section 2.3.3 and a non-return catch 2.3.4. Near the proximal end of the support body 2 two resilient snap arms 2.6 for interacting with the outer body 3 are arranged. The resilient snap arms 2.6 initially engage the outer body 3 near its distal end in such a manner that the outer body 3 and the support body 2 are axially coupled unless a first detent force is applied, which deforms the resilient snap arms 2.6 so that the outer body 3 decouples from the support body 2 and can move relative to the support body 2 in the distal direction D.

Figure 6:
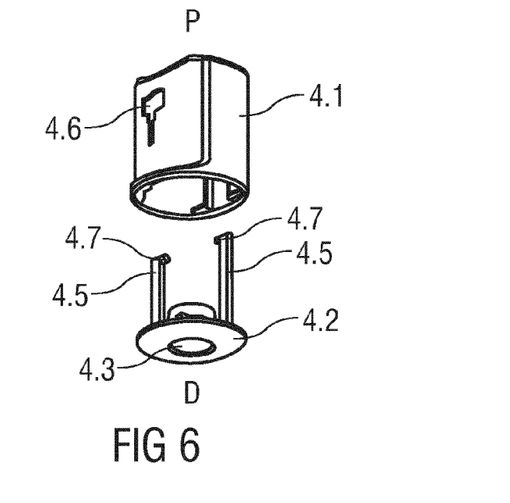
FIG. 6 is an exploded perspective view of the needle shield.

FIG. 6 is an exploded perspective view of the needle shield 4. The needle shield 4 comprises a tubular body section 4.1 and a cap part 4.2 with a central opening 4.3. The cap part 4.2 is engaged to the body section 4.1 by a snap fit 4.4 (cf. FIG. 3) thus preventing relative axial movement. Two resilient retaining clips 4.5 with a respective inward protrusion 4.7 are arranged on the cap part 4.2. The inward protrusions 4.7 engage the guiding track 2.3 in the support body 2 so as to restrict relative axial movement between the needle shield 4 and the support body 2. A protective needle boot (not illustrated) may be positioned in and/or through the central opening 4.3 of the cap part 4.2 before and after an injection. The cap part 4.2 is rotationally locked to the body section 4.1. This may be achieved by the cap part 4.2 having a non-circular, e.g. elliptical cross section engaging in a corresponding opening in the body section 4.1.

Figure 7:
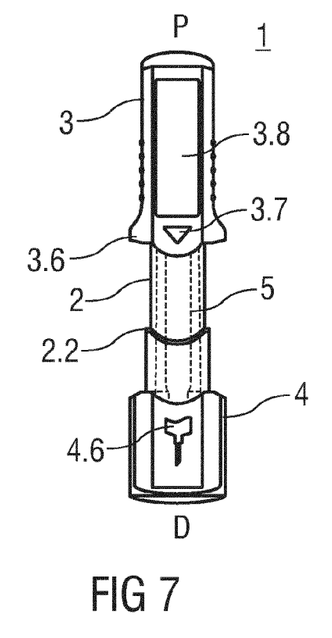
FIG. 7 is a lateral view of the drug delivery device prior to an injection.

FIG. 7 is a lateral view of the drug delivery device 1 prior to an injection. The outer body 3 is fully extended in the proximal direction P from the support body 2. The needle shield 4 is fully extended from the support body 2 in the distal direction D. The injection needle 6 is in a retracted position within the needle shield 4. The needle shield spring 9 is relaxed. In this situation the inward protrusion 4.7 is located distally from the distal inclined section 2.3.1 of the guiding track 2.3 so that the resilient retaining clips 4.5 are also relaxed.

Figure 8:
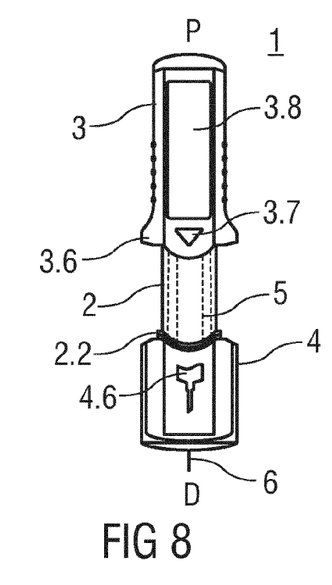
FIG. 8 is a lateral view of the drug delivery device during needle insertion.

A user may grab the outer body 3 and push the proximal end of the needle shield 4 against an injection site, e.g. a patient's skin. The force from the user's hand is resolved through the outer body 3, the resilient snap arm 2.6, the support body 2, the inclined section 2.3.1 of the guiding track 2.3 and the retaining clips 4.5 into the needle shield 4. The retaining clips 4.5 engaging the inclined section 2.3.1 of the guiding track 2.3 provide a second detent force which has to be overcome in order to move the needle shield 4 against the support body 2. As the user applies a sufficiently high force exceeding the second detent force the needle shield 4 is moved in the proximal direction P with respect to the support body 2 and all other parts of the drug delivery device 1 thereby also compressing the needle shield spring 9 so that the drug delivery device 1 arrives in a state as illustrated in FIG. 8. At the same time, the retaining clips 4.5 are deflected in a first tangential direction T1 by the inclined section 2.3.1 and the inward protrusions 4.7 travel up the longitudinal section 2.3.2 in the proximal direction P. Once the inward protrusion 4.7 has travelled proximally beyond the longitudinal section 2.3.2 the retaining clips 4.5 are no longer deflected. Hence, they will relax into a position proximally from the proximal inclined section 2.3.3 so the inward protrusion 4.7 is prevented from travelling the same way back on subsequent extension of the needle shield 4. The first detent force is greater than the sum of the second detent force and the counteracting force of the needle shield spring 9 at full depression of the needle shield 4 such that on application of the drug delivery device 1 against the patient's skin the needle shield 4 always moves prior to the outer body 3 relative to the support body 2. This movement is opposed by the friction force of the injection needle 6 when penetrating the skin. The needle insertion depth is defined by the needle shield 4 abutting the indicator ring 2.2. The mating surfaces of the indicator ring 2.2 and the needle shield 4 visually and haptically indicate to the user that they are intended to be pushed completely together in order to correctly apply the drug delivery device 1.

Figure 9:
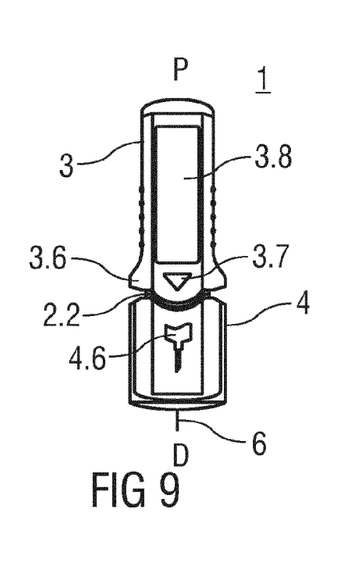
FIG. 9 is a lateral view of the drug delivery device at the end of injection.

Once insertion depth has been reached, further application of force onto the outer body 3 in excess of the first detent force results in deformation of the resilient snap arms 2.6 so that the outer body 3 decouples from the support body 2 and moves relative to the support body 2 in the distal direction D thus also moving the stopper 7 within the syringe barrel 5 so that the drug is displaced from the cavity through the injection needle 6. Near the end of the injection the stopper 7 bottoms out in the syringe barrel 5. At the same time the outer body 3 abuts the indicator ring 2.2 so that the drug delivery device 1 arrives in a state as illustrated in FIG. 9. The mating surfaces of the indicator ring 2.2 and the outer body 3 visually and haptically indicate to the user that they are intended to be pushed completely together in order to correctly apply the drug delivery device 1.

Figure 10:
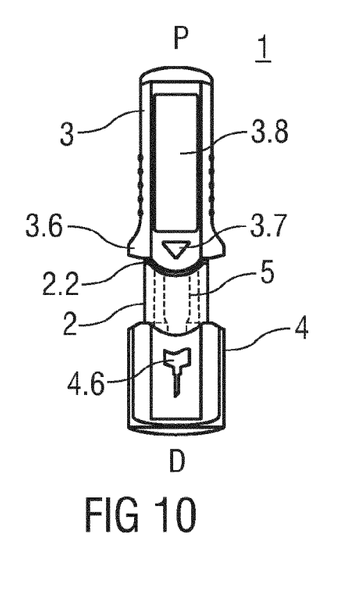
FIG. 10 is a lateral view of the drug delivery after needle refraction.

If the user removes the drug delivery device 1 from the injection site the needle shield 4 is no longer pushed against the skin and is hence extended in the distal direction D relative to the other components of the drug delivery device 1 by the needle shield spring 9 such that the injection needle 6 arrives fully inside the needle shield 4 as illustrated in FIG. 10. During this movement the inward protrusion 4.7 engages the proximal inclined section 2.3.3 and is deflected in a second tangential direction T2 opposed to the first tangential direction T1. Once the inward protrusion 4.7 has traveled distally beyond the proximal inclined section 2.3.3 the retaining clips 4.5 are no longer deflected. Hence, they will relax into the catch 2.3.4 thus locking the needle shield 4 in position relative to the support body 2. The inward protrusion 4.7 and the retaining clips 4.5 are neither accessible for the user nor can they be deflected out of the catch 2.3.4 in any other way. Hence, the needle shield 4 is prevented from being depressed once more without destroying the drug delivery device 1.

The end of the outer body 3 coupled to the support body 2 may comprise a radially outwards directed flange 3.6 thus improving ergonomics when applying the drug delivery device 1.

In an exemplary embodiment a direction indicator 3.7 designed as a profiled cavity or concavity in the surface of the outer body 3 is arranged in the range of the flange 3.6.

The needle shield 4 may likewise comprise a direction indicator 4.6.

A label retaining recess 3.8 may be arranged in the outer body 3 for receiving a label which may be customized to the drug to be delivered and/or to the provider of the drug.

Figure 11:
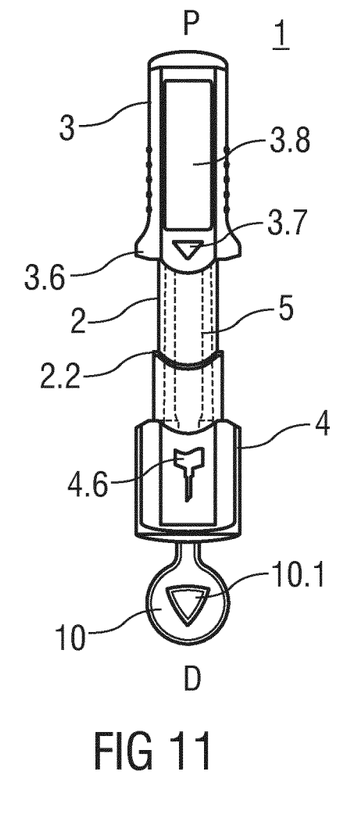
FIG. 11 is a schematic view of the drug delivery device with a boot remover for removing the protective needle boot prior to an injection.

FIG. 11 is a schematic view of the drug delivery device 1 with a boot remover 10 for removing the protective needle boot prior to an injection. The boot remover 10 may be arranged to engage the needle boot by friction or by means of barbs. The boot remover 10 comprises a handle extending from the opening 4.3 for facilitating boot removal. A direction indicator 10.1 may be provided on the boot remover 10 for indicating the direction in which the user has to move the boot remover 10 for removing the protective needle boot.

The invention claimed is:

1. A drug delivery device for setting and dispensing a dose of a drug, comprising:
   a support body having a first end defining a first opening and a second end defining a second opening, the support body configured to retain a syringe barrel sealed by a stopper slidably disposed therein along an axial direction and adapted to have an integrated needle or to be coupled with a needle assembly,
   a needle shield adapted to be coupled to one of the first and second ends of the support body, the needle shield being slidably disposed on the support body and keyed to the support body for preventing relative rotation,
   a guiding track defined on the support body,
   a resilient retaining clip arranged on the needle shield, the retaining clip being deflectable by the guiding track such that the retaining clip follows a first path when the needle shield is depressed from an extended position to a retracted position for needle extension, and such that the retaining clip follows a different second path when the needle shield is extended, and
   a non-return catch is arranged for catching the retaining clip at the end of the second path, the retaining clip being configured to:
      deflect in a first tangential direction and relax in a second tangential direction into a non-deflected position while moving along the first path when the needle shield is pushed against an injection site and retracts into the retracted position, and
      deflect in the second tangential direction and relax into the non-deflected position while moving from the second path into the catch when the needle shield is removed from the injection site and extends into the extended position.

2. The drug delivery device according to claim 1, wherein the second path is defined by a proximal inclined section of the guiding track for deflecting the retaining clip from the non-deflected position in the second tangential direction while the retaining clip moves along the second path, wherein the catch is arranged distally from the proximal inclined section in a manner allowing the retaining clip to relax in the first tangential direction into the catch.

3. The drug delivery device according to claim 1, wherein the first path is defined at least by a distal inclined section of the guiding track for deflecting the retaining clip in the first tangential direction away from the non-deflected position while the retaining clip moves along the first path.

4. The drug delivery device according to claim 3, wherein a longitudinal section is arranged proximally from the distal inclined section for defining the first path.

5. The drug delivery device according to claim 1, wherein an outer body is adapted to be coupled to the other of the first end and the second end of the support body opposite to the needle shield, the outer body being slidably disposed on the support body.

6. The drug delivery device according to claim 5, further comprising a first detent mechanism configured to constrain movement of the outer body relative to the support body by opposing this movement with a first detent force.

7. The drug delivery device according to claim 6, wherein the guiding track and the retaining clip form a second detent mechanism configured to constrain movement of the needle shield relative to the support body by opposing this movement with a second detent force.

8. The drug delivery device according to claim 7, wherein the second detent mechanism comprises at least a distal inclined section of the guiding track to deflect the retaining clip in the first tangential direction.

9. The drug delivery device according to claim 7, wherein the first detent force is greater than a sum of the second detent force and a counteracting force of a needle shield spring arranged to bias the needle shield against the support body.

10. The drug delivery device according to claim 5, wherein the second end of the support body defines a centered outer indicator ring arranged to limit movement of the outer body with respect to the support body and to limit movement of the needle shield with respect to the support body.

11. The drug delivery device according to claim 10, wherein the outer indicator ring is curved.

12. The drug delivery device according to claim 11, wherein the other of the first end and the second end of the outer body coupled to the support body comprises a radially outwardly directed flange, wherein a direction indicator designed as a profiled cavity or concavity in the surface of the outer body is arranged proximate the radially outwardly directed flange.

13. The drug delivery device according to claim 5, comprising a plunger rod coupled to the stopper, wherein a proximal portion of the plunger rod is adapted to be coupled to the outer body.

14. The drug delivery device according to claim 1, wherein the needle shield comprises a direction indicator.

15. The drug delivery device according to claim 1, wherein ends of the outer body and the needle shield coupled to the support body have mating surfaces.

16. The drug delivery device according to claim 1, wherein the needle shield comprises a tubular body section and a cap part, and the retaining clip extends proximally from the cap part through the tubular body section.

17. The drug delivery device according to claim 1, wherein the retaining clip comprises a protrusion configured to engage the guiding track.

18. The drug delivery device according to claim 17, wherein:
   the support body is slidably disposed within the needle shield, and
   the protrusion extends inwardly from the retaining clip to engage the guiding track of the support body.

19. The drug delivery device according to claim 17, wherein the protrusion and the retaining clip are positioned such that the needle shield prevents access to the protrusion and the retaining clip by a user after the needle shield is subsequently extended.

* * * * *